United States Patent

Sullivan et al.

[11] Patent Number: 6,116,076
[45] Date of Patent: Sep. 12, 2000

[54] METHOD FOR TESTING STATIC AND KINETIC FRICTIONAL COEFFICIENTS OF A SHEET MATERIAL

[75] Inventors: John L. Sullivan, Ft. Salonga; Jeffrey J. Bott, Setauket; Jacek A. Eubig, Floral Park; John S. Fortunato, Holbrook, all of N.Y.

[73] Assignee: Testing Machines, Inc., Islandia, N.Y.

[21] Appl. No.: 09/103,000

[22] Filed: Jun. 22, 1998

Related U.S. Application Data

[62] Division of application No. 08/871,515, Jun. 9, 1997.

[51] Int. Cl.⁷ .................................................. G01N 19/02
[52] U.S. Cl. ................................................................ 73/9
[58] Field of Search .............................................. 73/9, 10

[56] References Cited

U.S. PATENT DOCUMENTS

| | | | |
|---|---|---|---|
| 4,081,989 | 4/1978 | Majcherczyk | 73/9 |
| 4,187,714 | 2/1980 | Cox et al. | 73/9 |
| 4,580,675 | 4/1986 | Boltrek | 73/9 X |
| 4,798,080 | 1/1989 | Brungraber | 73/9 |
| 4,813,266 | 3/1989 | Nash | 73/9 |
| 4,895,015 | 1/1990 | English | 73/9 |
| 5,107,448 | 4/1992 | Nash | 73/9 X |
| 5,245,856 | 9/1993 | Pazzaglia et al. | 73/9 |
| 5,490,410 | 2/1996 | Markstrom | 73/9 |
| 5,734,088 | 3/1998 | Gunderson | 73/9 |
| 5,907,090 | 5/1999 | Gunderson | 73/9 |

FOREIGN PATENT DOCUMENTS

| | | | |
|---|---|---|---|
| 297 07 408 U1 | 7/1997 | Germany. | |
| WO 91/15763 | 10/1991 | WIPO. | |

OTHER PUBLICATIONS

Working Draft of Article "Papers and Boards, Determination of the Coefficients of Static and Kinetic Friction, Horizontal Plane Method", by Fellers and Gunderson, dated Jul. 20, 1995, 11 pages.

Report Entitled "Paper Friction–Influence of Measurement Conditions", prepared by Johansson, et al., prepared prior to Jul. 26, 1995, cover sheet + pages 1–12.

Draft of ISO Standard—Reference No. ISO/TC6/SC 2 N 1468, dated Apr. 11, 1996. Entitled Paper and Board–Determination of the Coefficients of Static and Kinetic Friction—Horizontal Plane Method cover page + pages 1–25.

*Primary Examiner*—Thomas P. Noland
*Attorney, Agent, or Firm*—Anthony J. Casella; Gerald E. Hespos; Michael J. Porco

[57] ABSTRACT

A horizontal plane frictional coefficient testing apparatus and methods are provided which include a substantially horizontal planar platen having two spaced, parallel movable rails. The rails are actuated by a motor adapted for reversibly raising and lowering the rails relative to the platen. A sled of predetermined weight is also provided having a central body and two pairs of outwardly extending axles, with each pair of axles being of equal length and formed with a wheel at the end thereof. The wheels of the sled are formed for engagement with the rails and engagement of the wheels with the rails locates the sled generally parallel to the rails. In operation, a sample of sheet material is fixed to the sled and the sled is placed on the rails, with the rails being in a raised position. Subsequently, the rails are lowered to gently place the sled onto the platen or a test medium fixed to the platen. A drive arm is included with the apparatus for pulling the sled relative to the platen at various rates of translation. A load sensor mounted on the drive arm measures in real time the force applied to the sled during the course of the test. The data collected by the load sensor is transmitted to a central processing unit which calculates the coefficients of friction. A timing mechanism may be provided to monitor the dwell time of the sled on the platen prior to initiation of the tests. Also, a semi-rigid coupling may be used to connect the sled to the drive arm.

12 Claims, 4 Drawing Sheets

METHOD FOR TESTING STATIC AND KINETIC FRICTIONAL COEFFICIENTS OF A SHEET MATERIAL

This application is a divisional of U.S. patent application Ser. No. 08/871,515, filed on Jun. 9, 1997, which is now pending.

BACKGROUND OF THE INVENTION

1. Field of the Invention

This invention relates to apparatus and methods for testing static and kinetic frictional coefficients of sheet material and, more particularly, an automated horizontal plane apparatus for testing static and kinetic frictional coefficients of sheet material and methods related thereto.

2. Description of the Prior Art

It can be appreciated that the determination of frictional characteristics of sheet materials, such as paper, film, rubber, plastics, wood, linoleum, and coatings, is crucial to evaluate the workability of the sheet materials in processes and by the end consumer. For example, paper photocopying machines are formed with rollers and paper feeding mechanisms which are designed to cooperatively feed sheets of paper having frictional coefficients within certain predetermined ranges. If the frictional coefficients are outside of these ranges, the photocopying machine may fail to feed the paper sheets or may feed the paper sheets irregularly. As a second example, linoleum sheets used as flooring must be formed with certain frictional characteristics which will allow a person to comfortably and safely walk thereupon.

Horizontal plane testing apparatus have been developed in the prior art to test static and kinetic frictional coefficients of sheet materials. The prior art devices include a horizontal platen with a clamping mechanism for rigidly fixing a sample of the sheet material to the platen. Typically, frictional coefficient testing apparatus are used to test the frictional coefficients between two samples of the same sheet material, although the frictional coefficients between two different sheet materials may also be tested. A second sample of sheet material is secured to a planar face of a sled. The sled is a generally parallelepiped shaped block having a predetermined weight. In the prior art, the sled is manually placed on the platen, with the two samples of sheet material being in face-to-face engagement, at one end of the first sample of sheet material. The sled is driven across at least a portion of the length of the first sample of sheet material at a constant speed along a single linear axis, and a load cell is coupled to the sled to measure the force required at all times to drive the sled across the length of the sheet material. A data acquisition system receives data measured by the load cell and calculates static and kinetic coefficients of friction for the interface of the two samples of sheet material. The static coefficient is an indicator of the degree of force required to initially move or "slip" the sled from a stationary position in a single coordinate direction, and, thus, it is calculated during the initial portion of the test, with the sled resting motionless on the platen. The value of the static coefficient is obtained by dividing the amount of force required to initially move the sled by the weight of the sled. In contrast, the kinetic coefficient is an indicator of the degree of force required to continue movement of the sled in a single coordinate direction, with the sled already being in motion. During the test, the kinetic coefficient may be determined once the sled is in motion and is calculated by dividing the amount of force required to continue movement of the sled by the weight of the sled.

An example of a prior art horizontal plane static and kinetic friction coefficient testing apparatus is manufactured and sold under the tradename "MONITOR/SLIP & FRICTION™" by Testing Machines, Inc. of Islandia, N.Y.

The prior art apparatus suffers from several drawbacks. First, the manual placement of the sled onto the platen results in testing errors and lack of testing repeatability due to varying forces being applied to the interface of the tested samples of sheet materials by an operator or operators of the apparatus. A slight difference in the degree of force applied in placing the sled onto the platen, greater or smaller, may translate to respectively greater or less meshing of the engaged surfaces of the samples, with corresponding increases or decreases in the measured values of the static frictional characteristics of the samples. Consequently, errors are created in measured data. Furthermore, even with an apparatus accurately measuring coefficients, the magnitude of the frictional coefficients will vary from test to test of the same samples due to the differences in pressures applied in placing the sled for each test. As such, the determination of the actual coefficients of a sheet material is quite difficult, requiring repeated testing of the same sheet material and intense scrutiny of such test results. Thus, there is a need for a testing apparatus which can measure static and kinetic frictional coefficients of a sheet material with repeated accuracy. It should be noted that absolute test repeatability is not required where exact test results are duplicated; however, test results should repeat within a statistically acceptable range. As used herein, "repeatable" and "repeatability", respectively, refer to test results obtained, and the ability to obtain test results, respectively, from the same samples which fall within statistically acceptable ranges of each other.

Second, manual placement of the sled onto the platen may result in misalignment of the sled relative to the platen. Since the force used to determine the static and kinetic frictional coefficients is linearly applied to the sled along a single axis, to obtain repeatable test measurements of a static frictional coefficient, the sled must be aligned in the same manner relative to the linear axis of the force for each test. Manual placement of the sled often results in misalignment, with attendant distorted results and lack of test repeatability. Also, the linear force is typically applied through a single point coupling with the sled. If the sled is not fully coaxially aligned with the axis of the linear force, the coupling acts as a fulcrum about which the sled rotates slightly into alignment with the linear axis during initial movement. The rotational motion of the sled relative to the platen generates resistive frictional forces in two coordinate directions, one coordinate direction being parallel to the linear axis and the second coordinate axis being perpendicular to the linear axis. Since the coefficients of friction are determined relative to the degree of force required to move the sled in one coordinate direction, the additional frictional forces generated in the second coordinate direction distort the test results. It can be appreciated that manual placement of the sled onto the platen often results in misalignment of the sled relative to the platen and subsequent slight rotational movement of the sled, resulting in a lack of repeatability in tests and inaccurate frictional coefficient measurements.

Third, a mechanism to control the dwell time of the sled on the platen relative to the actual start of the test is not present in the prior art apparatus. Once the sled is manually placed on the platen, the prior art apparatus must be manually actuated. However, the dwell time, the amount of time the sled rests on the platen prior to initiation of a test, affects the outcome of the test. With certain materials, "blocking", which is additional resistance to movement beyond friction, may occur as a result of molecular adherence between the tested materials caused by excessive dwell time. During such tests, forces applied to the sled must overcome not only friction, but also molecular adherence, to move the sled and, consequently, test results will be distorted. If there is an inadequate amount of dwell time, air trapped between the two samples of sheet material may not have an opportunity to evacuate, and a layer of air may be entrapped between the two samples during testing. The layer of air will act as a cushion and lessen the frictional forces generated between the two samples. Attempts have been made in the prior art to manually monitor dwell time to achieve repeatability of test results. As with the manual placement of the sled onto the platen, manual measurement of the dwell time is affected by human error, resulting in a failure to achieve testing repeatability.

Fourth, prior art horizontal plane frictional coefficient testing apparatus are configured to drive the sled during the course of the test at a single speed from initiation to completion. Each test run includes two portions, an initial static coefficient test portion and a subsequent kinetic coefficient test portion. The simultaneous end of the first portion of the test and the beginning of the second portion of the test is an instantaneous point in time at which the sled initially moves relative to the platen. The use of a constant test speed is appropriate for determining the kinetic coefficient of friction, however, the constant rate may lead to inaccuracies in determining the static coefficient of friction. With the application of the constant rate of speed from initiation of the test, a jolt or shock is applied to the sled initially which may distort force readings collected during the static coefficient phase of the test. Also, with a constant speed test, the force is applied to the sled with a constant rate. Since the capture of data relating to the instantaneous point of initial movement of the sled is essential to determining the static coefficient of friction, a slow speed, and thus a slow rate of applying force, is preferred to ensure accurate measurement of past data. However, with the amount of time to perform a test also being a factor, apparatuses are typically configured to run at a constant speed which generates a rate of force application greater than the aforementioned preferred rate. Repeated test runs at a constant rate slow enough to ensure accurate static frictional coefficient measurements may be overall too time-consuming in a commercial environment.

Fifth, prior art apparatus utilize rigid coupling systems which are not adaptable to the two portions of the testing procedure. A rigid coupling is preferred for the kinetic coefficient testing portion which allows constant transmission of the driving force to the sled, whereas, in contrast, some elasticity is preferred in the coupling for the static coefficient portion of the test. An elastic coupling would allow a load to be applied to the sled gradually, rather than abruptly.

A sixth drawback in the prior art is the rearward translation of the sled relative to the platen due to manual placement and/or removal of the sled from the platen. As described above, prior to a test run in the prior art, the sled is manually placed onto the platen. However, often the sled is manually placed on the platen with subsequent movement of the sled in an opposite direction from the direction in which the sled is to be translated during the test run. As a result, the friction between the interengaging faces of the samples of sheet material causes the grain of the surfaces of the samples to be urged into the opposite direction. Since several tests are often performed on the same samples of sheet material, the disturbed grain of the sample surfaces undermines repeatability in test results. Furthermore, manual removal of the sled from the platen after a test run may also cause rearward movement of the sled relative to the platen and further disruption of the grain of the sample surfaces. To enhance test repeatability, "back sliding" of the sled relative to the platen should be avoided.

It is an object of the subject invention to provide a horizontal plane frictional coefficient testing apparatus which overcomes the shortcomings of the prior art devices and measures static and kinetic frictional coefficients with repeatability.

Also, it is an object of the subject invention to provide a horizontal plane frictional coefficient testing apparatus which provides for automated reversible lifting and lowering of a sled.

It is also an object of the subject invention to provide a frictional coefficient testing apparatus which ensures proper alignment of the sled relative to the platen of the apparatus.

It is a further object of the subject invention to provide a horizontal plane frictional coefficient testing apparatus which operates at more than one speed during a single test and is provided with a semi-rigid coupling for the sled which reacts to the operating speed of the apparatus.

Yet another object of the subject invention is to provide an apparatus which monitors dwell time of the sled on the platen and initiates test runs at the lapse of predetermined dwell times.

It is a further object of the subject invention to provide a horizontal plane frictional coefficient testing apparatus which prevents translation of the sled before and after a test run in a direction opposite the testing direction.

SUMMARY OF THE INVENTION

The above-stated objects are met by a new and improved horizontal plane frictional coefficient testing apparatus. The apparatus includes a substantially planar horizontal platen formed with two spaced, parallel movable rails and a clamping mechanism. The rails are actuated by a motor adapted for reversibly raising and lowering the rails relative to the platen. A sled is provided having a central body, resembling the sleds of the prior art, and two pairs of outwardly extending axles, with one pair of the axles extending from each side of the sled being of equal length and with each axle having a wheel rotatably mounted to the end thereof. A drive arm is included with the apparatus for pulling the sled during a test run, which includes two phases: a static coefficient testing phase and a kinetic coefficient testing phase.

The wheels of the sled are formed for engagement with the rails. With the wheels engaging the rails, the sides of the sled are generally parallel to the rails. In operation, a sample of a sheet material is fixed to the sled. The frictional characteristics of the sample may be tested with respect to a test medium, which could be a second sample of sheet material fixed to the platen by the clamping mechanism or a liquid. Additionally, the frictional characteristics of the sample may be tested with respect to the bare platen, which acts as a test surface. The sled is placed on the rails, with the rails being in a raised position, and, subsequently, the rails are lowered to gently place the sled onto the sample clamped to the platen, in contact with the liquid or onto the bare platen. Automated lowering of the sled onto the sample/platen ensures repeated placement of the sled with the same degree of placement force, and the engagement of the wheels and rails ensures repeated proper alignment of the sled relative to the platen. A timing mechanism may be provided to measure dwell time from the moment the rails are lowered with the sled being placed on the sample/platen and to generate a signal to initiate the test run upon lapse of the predetermined dwell time.

Once the test run is initiated, a drive arm applies a driving force to the sled. The drive arm is coupled to the sled through a semi-rigid coupling. Specifically, the sled is formed with a downwardly directed coupling member formed to register with an inner channel of a tubular viscoelastic bushing disposed in an aperture in the drive arm. At the initiation of the test run, the coupling member is centrally located in the channel of the viscoelastic bushing, with no contact between the coupling member and the bushing. Upon actuation of the drive arm, the static coefficient testing phase begins, and the drive arm moves at a relatively slow constant rate. With movement of the drive arm, the coupling member comes into pressing contact with the bushing. The viscoelastic material of the bushing is selected such that slight deformation of the bushing is achieved due to the pressing contact of the coupling member thereon. As a result of the deformation of the bushing, although the drive arm is moving at a constant rate, force is gradually applied to the sled. A load sensor is mounted on the drive arm to collect real time force data with respect to the sled. The real time data collected by the load sensor is transmitted to a central processing unit for data evaluation. The length of time of the static coefficient testing phase of the test run is predetermined. The central processing unit is configured to initiate the kinetic coefficient testing phase of the test run, upon lapse of the predetermined length of time. In the kinetic coefficient testing phase of the test run, the speed of the drive arm is increased and maintained at the increased rate to the end of the test run. Real time data is continuously collected by the load sensor and evaluated by the central processing unit.

In this manner, the apparatus of the subject invention allows the static frictional coefficient phase of the test to operate at a relatively slow rate and the kinetic frictional coefficient phase of the test to operate at a faster rate, thereby allowing for proper data gathering within an acceptable test-taking time frame.

The load sensor measures force values over a number of positions as the sled translates the length of the test run. The central processing unit collects the measured data and calculates the frictional coefficients. When the sled approaches the end of the test run, the central processing unit actuates the reversible elevating mechanism of the rails, and the rails are raised into the upper position. The rails are caused to elevate with the sled moving forward, such that the sled continues to move forward with the rails being raised, and "back sliding" of the sled is altogether avoided.

The viscoelastic material of the bushing is selected such that slight deformation of the bushing is achieved during initiation of the test run, with the driving force being initially applied, and, once slightly deformed, the bushing is sufficiently rigid to prevent further deformation. Therefore, the viscoelastic bushing provides elasticity during the static frictional coefficient testing portion of the test run and substantial rigidity during the kinetic frictional coefficient portion of the test run.

In an alternative embodiment, an anti-skid arm may be hingedly connected to the drive arm. The anti-skid arm can be formed to cooperate with the sled to ensure proper alignment of the sled with the coupling member of the sled being centrally located in the channel of the viscoelastic bushing at the initiation of a test run. Also, the anti-skid arm can include guide pins for limiting misalignment of the sled during the test run.

Additionally, the platen may be provided with an inset heating mechanism which can raise the temperature of the platen and any test medium which may be disposed thereon. With the ability to heat the platen and the test medium, the apparatus of the subject invention does not only allow an operator to determine the effect of heat on the frictional characteristics of the sample of sheet material, but also the operator can generally observe the effect of heat on the sample.

These and other features of the subject invention will be better understood through an examination of the following detailed description and accompanying drawings.

DETAILED DESCRIPTION OF THE PREFERRED EMBODIMENTS

Referring generally to the FIGURES, an apparatus 10 is provided for testing the static and kinetic frictional coefficients of the interface of a test medium or a test surface and a sample of sheet material 14. In the first embodiment of the invention, the apparatus 10 is for testing the static and kinetic frictional coefficients of the interface between two samples of sheet material 12, 14. The samples 12, 14 may be of the same sheet material or, alternatively, of two different sheet materials. The apparatus 10 generally comprises a platen 16, a sled 18, a drive arm 20, a load sensor 22, and a central processing unit 24.

The platen 16 is generally planar and horizontal. The platen 16 must be horizontal so that the weight of the sled 18 generates a force normal to the platen 16. In calculating the frictional coefficients, it is assumed that the weight of the sled 18 is a normal force acting on the platen 16, and any misalignment of the platen 16 from a horizontal plane will distort the test results. The platen 16 is preferably formed with a rectangular shape. At one end of the platen 16, a clamp 26 is provided for rigidly securing the first sample of sheet material 12 to the platen 16. The clamp 26 may be of any conventional design. The FIGURES represent an exemplary embodiment of the clamp 26 wherein a clamp body 28 is provided which is pivotally mounted to pedestals 30, 32 by pivots 36. The clamp 26 further includes a biasing means (not shown) for urging edge 38 of the clamp body 28 into abutting contact with the platen 16. The edge 38 of the clamp body 28 is separated from the platen 16 by applying a pulling force to handle 40, which extends from the clamp body 28. The first sample of sheet material 12 is fixed to the platen 16 with the first sample 12 being interposed between the edge 38 of the clamp body 28 and the platen 16 and the edge 38 being biased toward the platen 16.

The platen 16 is also formed with a pair of spaced, parallel elongated slots 42, 44. A single rail 46, 48 is movably disposed in each of the elongated slots 42, 44 respectively. Reversible elevating and lowering means 50 is mechanically coupled to the rails 46, 48 to reversibly raise and lower the rails 46, 48 relative to the platen 16. The rails 46, 48 must be raised and lowered simultaneously.

Figure 1:
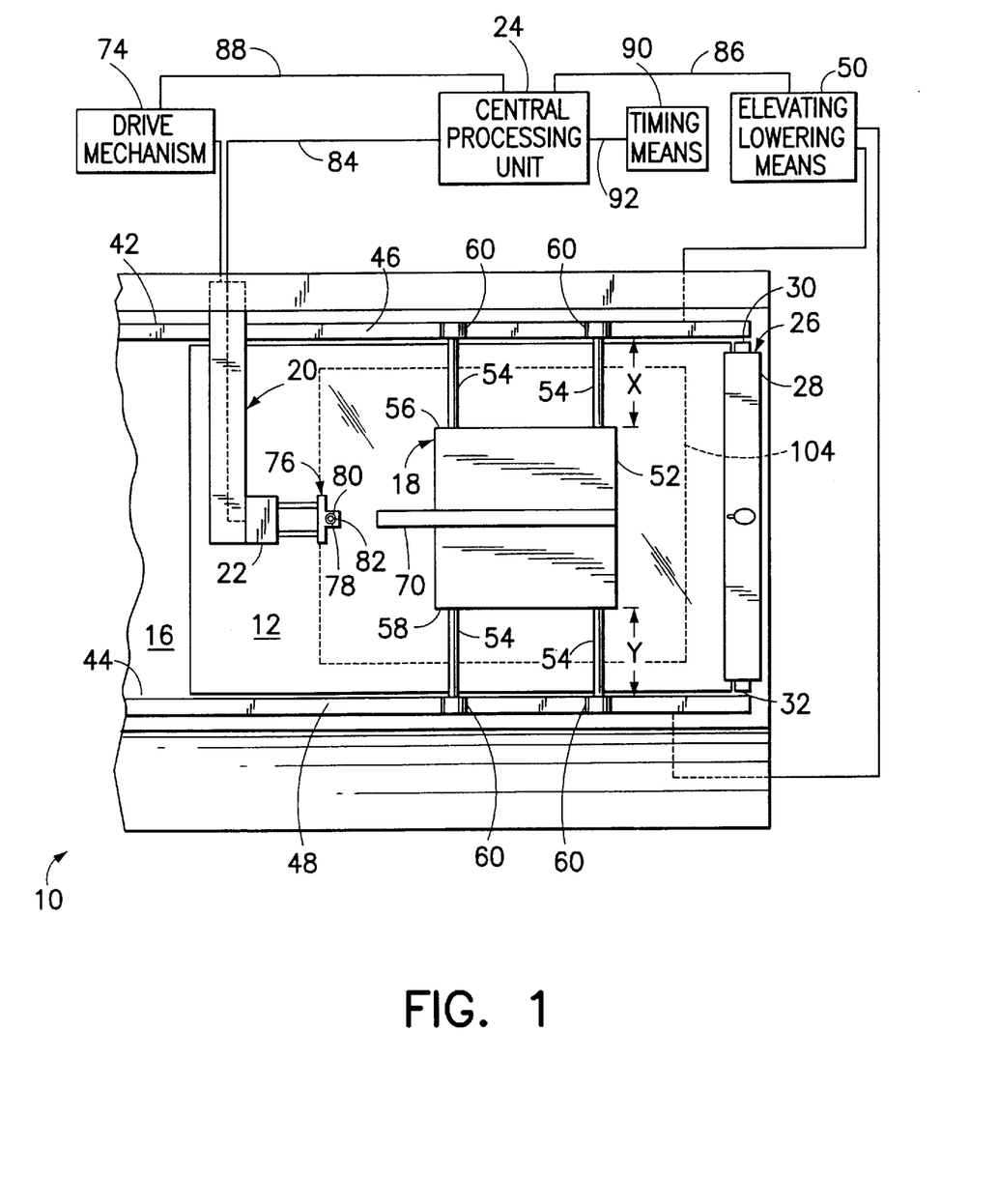
FIG. 1 is a top plan view of the first embodiment of the subject invention, parts of which are schematically illustrated.

The sled 18 is of a known weight and formed with a generally parallelepiped shaped central body 52 and a plurality of axles 54. As shown in FIG. 1, each of the axles 54 extending from one side 56, 58 of the sled 18 is of the same length. Referring to FIG. 1, the axles 54 extending from the side 56 of the sled are each formed with the length "x", whereas, the axles 54 extending from the side 58 are each formed with the length "y". All of the axles 54 may be formed with the same length, where length "x" equals length "y". The length or lengths of the axles 54 must be chosen such that the bridge 70 of the sled 18, described below, is coaxially aligned with the longitudinal axis along which force is applied to the sled 18 by the drive arm 20. Although the FIGURES show four of the axles 54 extending from the sled 18, any number of the axles 54 may be used with the sled 18. Preferably, an equal number of the axles 54 extend from the side 56 of the sled 18 as from the side 58.

Figure 4A:
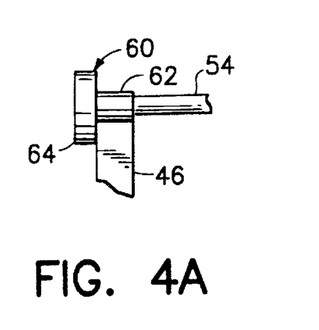
FIGS. 4a–4c are partial views of three separate embodiments of the wheels of the sled of the subject invention.
Figure 4B:
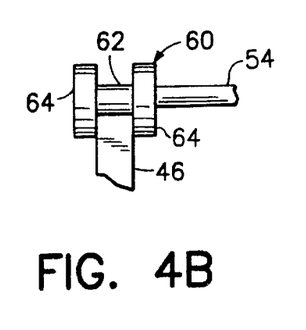
Figure 4C:
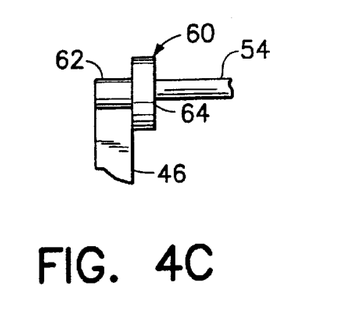

A wheel 60 is mounted to the end of each of the axles 54 and the wheels 60 are preferably rotatably mounted to the axles 54. The wheels 60 are preferably formed for rolling engagement with the rails 46, 48. As shown in FIGS. 4a–4c, each of the wheels 60 is formed with a central hub 62 and at least one circumferentially extending rim 64. The rims 64 of the wheels 60 collectively ensure that the hubs 62 maintain engagement with the respective rails 46, 48. Also, due to partial face-to-face contact of the rims 64 and the rails 46, 48, the rims 64 ensure repeatable alignment of the wheels 60 relative to the respective rails 46, 48, thus, ensuring repeatable alignment of the sled 18 relative to the platen 16. With the axles 54 being of the same length from each of the sides 56, 58 of the sled 18, the axles 54 will cause the sides 56, 58 of the sled 18 to be substantially parallel to the rails 46, 48. In this manner, the sled 18 may be repeatedly aligned in the same manner relative to the platen 16 so that under a driving force the sled 18 translates along a linear path and rotational movement, such as that found with prior art devices, is avoided.

The central body 52 of the sled 18 is also formed with a top surface 66 and a bottom surface 68. A bridge 70 is secured to the top surface 66 from which a coupling member 72 extends downwardly. The bottom surface 68 is substantially planar and formed to accommodate the second sample of sheet material 14. The axles 54 are located on the respective sides 56, 58 of the sled 18 such that with the sled 18 being disposed on a generally planar surface, such as the platen 16, the wheels 60 do not come into contact with the planar surface. Also, the axles 54 are located on the respective sides 56, 58 of the sled 18 to align the bottom surface 68 of the sled 18 in a generally parallel relationship to the platen 16 with the wheels 60 engaging the rails 46, 48.

The drive arm 20 is mechanically coupled to a drive mechanism 74. The drive mechanism 74 is configured to cause linear translation of the drive arm 20 at various rates of translation. The load sensor 22 is mounted to the end of the drive arm 20 with coupling 76 extending therefrom. The coupling 76 is formed with a coupling aperture 78 which houses a viscoelastic bushing 80 having an inner channel 82 dimensioned slightly larger than the coupling member 72 of the sled 18. The path along which the coupling aperture 78 travels during a test run defines the longitudinal axis along which force is applied to the sled 18. As described above, the bridge 70 is located to be generally coaxial with this axis. The coupling member 72 preferably is located on a point along the longitudinal center line of the bridge 70. Although not shown, alternatively, the coupling 76 may be formed with the coupling member 72, and the bridge 70 may be formed with the coupling aperture 78 having the viscoelastic bushing 80 being disposed therein. However, with this alternative embodiment, the coupling member 72 must extend away from the platen 16 to allow simultaneous placement of the sled 18 onto the rails 46, 48 and telescopic mating of the inner channel 82 of the bushing 80 with the coupling member 72 in a spaced relationship.

With the sled 18 being coupled to the drive arm 20 and translating relative to the platen 16 as described below, the load sensor 22 collects real time data of forces transmitted through the coupling 76 required to cause translation of the sled 18 relative to the platen 16. The real time data collected by the load sensor 22 is transmitted through connector 84 to the central processing unit 24 for real time evaluation. The weight of the sled 18 is input into the central processing unit 24 and the respective static and kinetic coefficients of friction are calculated using methods well known by those skilled in the art. The central processing unit 24 is also connected to the reversible elevating and lowering means 50 via connector 86 and the drive mechanism 74 via the connector 88. The central processing unit 24 is configured to control the reversible elevating and lowering means 50 and the drive mechanism 74.

Figure 2:
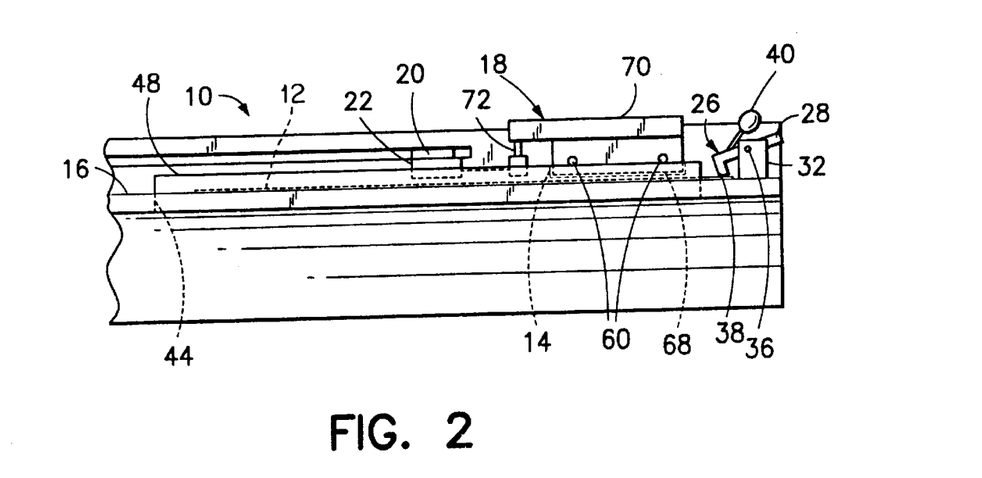
FIG. 2 is a side elevational view of the first embodiment of the subject invention with the rails and the sled being in a raised position.

In operation, the first sample of sheet material 12 is secured to the platen 16 by the clamp 26. The second sample of sheet material 14 is secured to the bottom surface 68 of the sled 18 using any conventional method known by those skilled in the art, such as clamping (not shown) or adhering (not shown). With the rails 46, 48 being in a raised position, as shown in FIG. 2, the sled 18, being of known weight, is placed onto the apparatus 10 with the wheels 60 engaging the rails 46, 48. The rims 64 of the wheels 60 respectively come into partial face-to-face engagement with the rails 46, 48. Simultaneously, the coupling member 72 is aligned to register with the inner channel 82 of the semi-rigid viscoelastic bushing 80. In this position, the second sample of sheet material 14 is maintained in a spaced, parallel relationship relative to the first sample of sheet material 12 fixed to the platen 16. Subsequently, the central processing unit 24 is activated, which actuates the reversible elevating and lowering means 50 and the rails 46, 48 are lowered relative to the platen 16. As the rails 46, 48 are lowered, the second sample of sheet material 14 comes into face-to-face engagement with the first sample of sheet material 12 fixed to the platen 16, and the coupling member 72 telescopically mates with the inner channel 82 of the semi-rigid viscoelastic bushing 80. The coupling member 72 is disposed to be in the inner channel 82 such that there is no contact between the coupling member 72 and the semi-rigid viscoelastic bushing 80.

Figure 3:
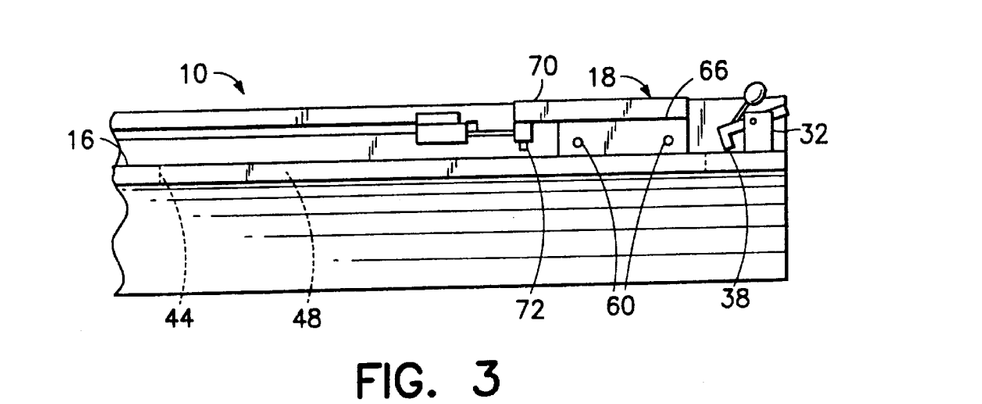
FIG. 3 is a side elevational view of the first embodiment of the subject invention with the rails being in a lowered position and the sled resting on the platen.

As shown in FIG. 3, with the rails 46, 48 being in a completely lowered position, the sled 18 rests on the platen 16 with the axles 54 and the wheels 60 being spaced from the platen 16. Thereafter, the central processing unit 24 actuates the drive mechanism 74 to cause the drive arm 20 to translate relative to the platen 16. A timing means 90 may be provided to measure the dwell time of the sled 18 on the platen 16. The timing means 90 can be connected to the central processing unit 24 through a connector 92 and adapted to receive a signal from the central processing unit 24 indicating the placement of the sled 18 onto the platen 16, and transmitting a signal to the central processing unit 24 after the lapse of a predetermined amount of dwell time. Alternatively, the timing means 90 may be formed integrally with the central processing unit 24, or, the central processing unit 24 may perform the functions of the timing means 90, thereby, obviating the need for the separate timing means 90.

As the drive arm 20 translates, force is transmitted to the sled 18 through the coupling 76. Initially, the drive mechanism 74 causes the drive arm 20 to translate at a slow constant rate. The translation of the drive arm 20 causes the coupling member 72 to press against the viscoelastic bushing 80. The viscoelastic material of the bushing 80 is chosen such that, under slight pressure, the viscoelastic material compresses relatively easily. Consequently, the initial force transmitted to the bushing 80 by the coupling member 72 is partially absorbed by compression of the viscoelastic material of the bushing 80. As greater force is applied to the bushing 80 by the coupling member 72, the viscoelastic material resists further compression and, at the point of contact between the coupling member 72 and the bushing 80, eventually becomes substantially rigid. As a result, although the drive arm 20 translates at a slow constant rate, the compression of the bushing 80 advantageously allows force to be initially applied to the coupling member 72 at a gradually increasing rate. The compression of the bushing 80 causes force to be absorbed, and, as the bushing 80 becomes fully compressed, force is directly transmitted from the drive arm 20 to the sled 18, via the coupling member 72.

The drive arm 20 will linearly translate at the slow constant rate for a predetermined period of time, which is the static coefficient testing phase of the test run. The static coefficient testing phase of the test run requires relatively little time. For example, with the drive arm 20 translating at a rate of 0.4 inches/minute, the static testing phase of the test run may only require several milliseconds, during which the sled 18 "slips" into motion. It can be appreciated that real time evaluation of the static coefficient of friction is not practicably feasible. Thus, the time period for the static coefficient testing phase is predetermined by the user of the apparatus 10. If the static coefficient of friction of the interface of the samples 12, 14 is completely unknown, the user of the apparatus 10 may iteratively test the samples 12, 14 using various lengths of time for the static coefficient testing phase of each of the runs, until the static coefficient of friction is determined with repeatable accuracy. If the apparatus 10 is used in an application where the static coefficient of the samples 12, 14 is known, such as with random quality assurance tests, the length of the static coefficient phase of the test run is set to ensure capture of static coefficient test data.

During the static coefficient testing phase of the test run, as described above, force is applied to the sled 18 gradually. As the force applied to the sled 18 is slowly increased, the sled 18 is eventually caused to linearly translate relative to the fixed first sample of sheet material 12 and the platen 16. The amount of force required to initially move the sled 18 is determinative of the static coefficient of friction of the interface of the two samples of sheet material 12, 14. Data of force measurements applied to the sled 18 are transmitted from the load sensor 22 to the central processing unit 24 via the connector 84. The central processing unit 24 evaluates the collected force data and determines the point of initial movement of the sled 18 by identifying the greatest force applied to the sled 18. The value of the greatest force is used by the central processing unit 24 to calculate the static coefficient of friction. Once the predetermined length of the static coefficient testing phase lapses, the kinetic coefficient testing phase of the test run is initiated, whereby the central processing unit 24 transmits a signal to the drive mechanism 74 to increase the rate of translation of the drive arm 20 and to constantly maintain the increased rate of translation of the drive arm 20 to the end of the test run. The load sensor 22 continues to measure forces applied to the sled 18, and the collected force data is evaluated by the central processing unit 24 to determine the kinetic coefficient of friction.

Due to the elasticity of the viscoelastic material of the bushing 80, the degree of rigidity at the interengagement of the coupling member 72 and the bushing 80 is reactive to the different phases of the test run. During initiation of the static coefficient testing phase, the coupling member 72 presses against the bushing 80. The viscoelastic material of the bushing 80 is chosen such that, with initial application of the force, the viscoelastic material slightly compresses due to pressure generated by the coupling member 72 pressing against the bushing 80. The slight compression of the elastic bushing 80 allows force to be initially gradually applied to the sled 18 and avoids a sudden application of force, which may cause a jolt or shock, to the sled 18 and distort test results during the static coefficient testing phase. The compressibility of the viscoelastic material of the bushing 80 is limited such that, once slightly compressed, the viscoelastic material of the bushing 80 becomes substantially rigid. Thus, during the kinetic coefficient testing phase, the bushing 80, being substantially rigid at the point of engagement with the coupling member 72, directly transmits all of the force acting on the drive arm 20 through the coupling 76 to the coupling member 72 and, in turn, to the sled 18. Consequently, the bushing 80 allows the coupling 76 to be semi-rigid and reactive to the initial static coefficient testing phase of the test and the subsequent kinetic coefficient testing phase of the test.

The length of the test run can be input into the central processing unit 24, as well as the rates of translation of the drive arm 20. As the sled 18 approaches the end of the test run, the central processing unit 24 transmits a signal via connector 86 to the reversible elevating and lowering means 50 to elevate the rails 46, 48 relative to the platen 16. As the sled 18 completes the test run, the rails 46, 48 engage the wheels 60 and the sled 18 is lifted from the platen 16. As the sled 18 is being lifted from the platen 16, the sled 18 continues to move in the testing direction. In this manner, "back sliding" of the sled 18 in a direction opposite the direction of the test is altogether avoided. With the rails 45, 48 being in a raised position, the sled 18 and the drive arm 20 may be reset for a subsequent test run.

Figure 8:
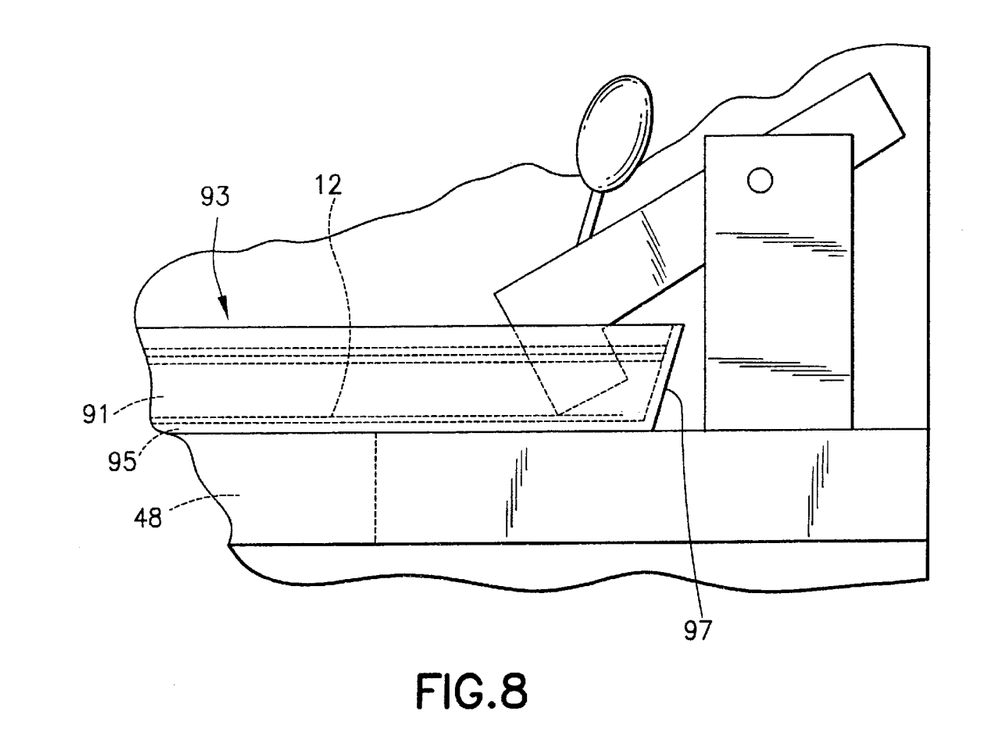
FIG. 8 is a partial side elevational view of the embodiment of the subject invention being provided with a pan for accommodating a liquid.

A liquid 91 may be interposed between the two samples of sheet material 12, 14. For example, the liquid 91 can be a lubricant to determine the effect of the lubricant on the frictional characteristics of the two samples of sheet material 12, 14. As shown in FIG. 8, a shallow pan 93 may be placed on the platen 16. The pan 93 is formed with a base 95 and a side wall 97 extending from the entire periphery of the base 95. The base 95 is dimensioned to accommodate the first sample of sheet material 12, and may be either secured to the platen 16 (not shown) or securely fixed to the platen 16 by the clamp 26. The features and the operation of the apparatus 10 otherwise is exactly as described above. Alternatively, in a second embodiment of the invention, the apparatus 10 may be used to measure the frictional characteristics of the interface of the sample of sheet material 14 and the liquid 91. To achieve such results, only the liquid 91 is provided in the pan 93, and the first sample of sheet material 12 is not required. In a third embodiment of the invention, the apparatus 10 can measure the frictional characteristics of the interface of the sample of sheet material 14 and the platen 16, which acts as the test surface. Although not shown in the FIGURES, the features and the operation of the apparatus 10 are exactly as described above, except the sled 18 with the sample of sheet material 14 is placed directly onto the bare platen 16.

Figure 5:
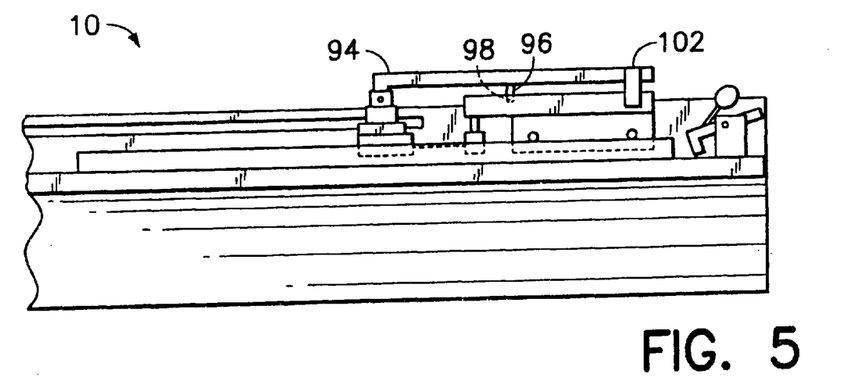
FIG. 5 is a side elevational view of the embodiment of the subject invention being provided with an anti-skid arm, wherein the rails and the sled are in a raised position.
Figure 6:
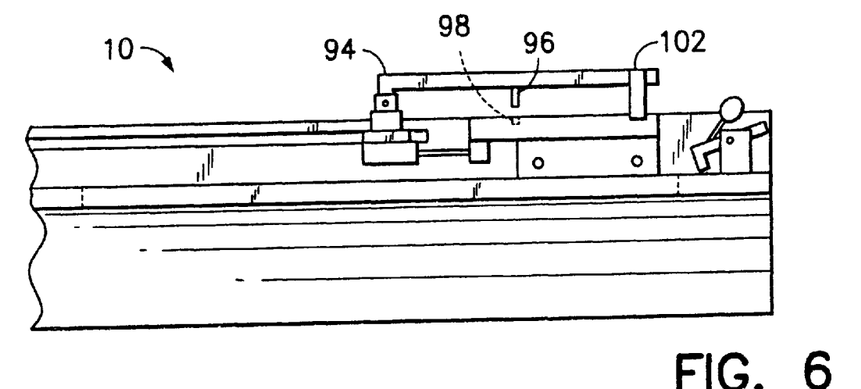
FIG. 6 is a side elevational view of the embodiment of the subject invention being provided with an anti-skid arm, wherein the rails are in a lowered position and the sled is resting on the platen.
Figure 7:
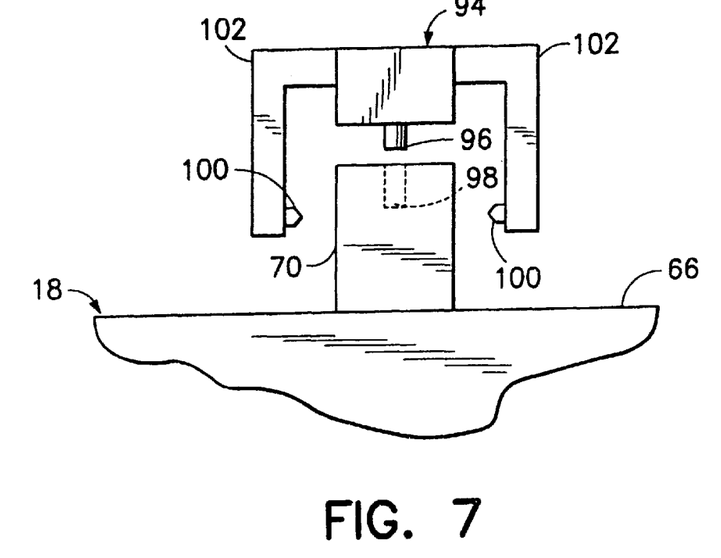
FIG. 7 is a partial rear elevational view of the embodiment of the subject invention being provided with an antiskid arm, wherein the bridge of the sled is interposed between the guide pins of the anti-skid arm.

Referring to FIGS. 5–7, an anti-skid arm 94 may be hingedly mounted to the drive arm 20 in any of the above-described embodiments. The anti-skid arm 94 may serve two functions. First, a locator pin 96 may extend from the underside of the anti-skid arm 94 and be located to register with a locator aperture 98 formed in the bridge 70 of the sled 18 with the anti-skid arm 94 being in a down position. The registration of the locator pin 96 and the locator aperture 98 ensures proper alignment of the sled 18 relative to the apparatus 10 with the coupling member 72 being aligned with the inner channel 82 of the viscoelastic bushing 80 to avoid contact therebetween. Preferably, the center of the coupling member 72 is aligned to coincide with the center of the inner channel 82. As shown in FIG. 6, with the rails 46, 48 being in a lowered position, there is no registration of the locator pin 96 and the locator aperture 98. The hinge connection of the anti-skid arm 94 maintains the arm 94 in a spaced relationship relative to the bridge 70 with the arm 94 being in a down position. In this manner, distortion of test results is avoided by ensuring application of force to the sled only through the interengagement of the coupling member 72 and the coupling 76.

The second function of the anti-skid arm 94 is to ensure linear movement of the sled throughout the test run. As shown in FIG. 7, inwardly directed guide pins 100 respectively extend from guide blocks 102. The guide pins 100 are located to be spaced from the bridge 70 under normal operation. However, non-linear translation of the sled 18 can be limited due to engagement of at least one of the guide pins 100 with the bridge 70. The degree of spacing between the guide pins 100 and the bridge 70 may be adjusted to increase or decrease the allowable range of non-linear translation of the sled 18.

As an additional feature, which can be used with any of the above-described embodiments, the platen 16 may be provided with a heating mechanism 104. Referring to FIG. 1, the heating mechanism 104 may be inset into the bottom surface of the platen 16. Although the heating mechanism 104 is only shown in the FIGURES with reference to the first embodiment, the heating mechanism 104 can be used with any embodiment of the invention. The heating mechanism 104 can be any conventional heating mechanism known by those skilled in the art. The heating of the platen 16 during a test run will enable an operator to not only determine the frictional characteristics of the interface between the sample of sheet material 14 secured to the sled 18 and the test medium or the test surface, but also the operator may observe the effects of heat on the sample of sheet material 14.

Although preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A method for determining static and kinetic frictional coefficients of the interface between a sample of a sheet material and a test medium, said method comprising:

fixing the test medium to a substantially horizontal platen;

fixing the sample of sheet material to a sled;

providing two spaced, parallel movable rails coupled to an automated reversible raising and lowering means for raising and lowering said sled relative to said platen;

lowering said sled onto said platen by lowering said parallel movable rails using said automated raising and lowering means such that the sample comes into engagement with the test medium;

translating said sled relative to said platen;

measuring the forces required to translate said sled relative to said platen; and calculating the frictional coefficients based on the measured forces and the weight of said sled.

2. A method as in claim 1, wherein the step of providing said parallel movable rails also includes providing automated alignment means for aligning said sled relative to said platen, wherein said sled includes a plurality of wheels formed for face-to-face engagement with said rails, and wherein the step of lowering said sled onto said platen also includes aligning said sled relative to said platen using said automated alignment means.

3. A method as in claim 1, further comprising the step of waiting a predetermined amount of time after the step of lowering said sled onto said platen and before the step of translating said sled relative to said platen.

4. A method as in claim 1, wherein the step of translating said sled relative to said platen includes translating said sled relative to said platen at more than one rate of translation.

5. A method as in claim 1, wherein the step of translating said sled relative to said platen includes translating said sled relative to said platen for a predetermined length, and wherein the method further includes the step of raising said sled from said platen by raising said parallel movable rails using said reversible raising and lowering means with said sled having translated said predetermined length, whereby raising said sled prevents inadvertent translation of said sled in an opposite direction.

6. A method as in claim 1, further comprising the step of heating said platen.

7. A method for determining static and kinetic frictional coefficients of the interface between a sample of a sheet material and a test surface, said method comprising:

providing a substantially horizontal platen which defines the test surface;

fixing the sample of sheet material to a sled;

providing two spaced, parallel movable rails coupled to an automated reversible raising and lowering means for raising and lowering said sled relative to said sled relative to said platen;

lowering said sled onto said platen by lowering said parallel movable rails using said automated raising and lowering means such that the sample comes into engagement with the test surface of said platen;

translating said sled relative to said platen;

measuring the forces required to translate said sled relative to said platen; and calculating the frictional coefficients based on the measured forces and the weight of said sled.

8. A method as in claim 7, wherein the step of providing said parallel movable rails also includes providing automated alignment means for aligning said sled relative to said platen, wherein said sled includes a plurality of wheels formed for face-to-face engagement with said rails, and wherein the step of lowering said sled onto said platen also includes aligning said sled relative to said platen using said automated alignment means.

9. A method as in claim 7, further comprising the step of waiting a predetermined amount of time after the step of lowering said sled onto said platen and before the step of translating said sled relative to said platen.

10. A method as in claim 7, wherein the step of translating said sled relative to said platen includes translating said sled relative to said platen at more than one rate of translation.

11. A method as in claim 7, wherein the step of translating said sled relative to said platen includes translating said sled relative to said platen for a predetermined length, and wherein the method further includes the step of raising said sled from said platen by raising said parallel movable rails using said reversible raising and lowering means with said sled having translated said predetermined length, whereby raising said sled prevents inadvertent translation of said sled in an opposite direction.

12. A method as in claim 7, further comprising the step of heating said platen.

* * * * *